United States Patent [19]

Suzuki

[11] 3,948,986

[45] Apr. 6, 1976

[54] ALPHA-HYDROXY OR ALKOXY ACID PREPARATION

[75] Inventor: Shigeto Suzuki, San Francisco, Calif.

[73] Assignee: Chevron Research Company, San Francisco, Calif.

[22] Filed: Jan. 20, 1975

[21] Appl. No.: 542,138

[52] U.S. Cl. ............ 260/535 R; 260/340.2; 260/413; 260/484 R; 260/488 F; 260/484 A

[51] Int. Cl.² .......................................... C07C 59/08

[58] Field of Search ................................ 260/535 R

[56] References Cited
OTHER PUBLICATIONS

Falbe, J. Carbon Monoxide in Organic Synthesis, Springer Verlag N.Y. 1970, p. 118.

*Primary Examiner*—Lorraine A. Weinberger
*Assistant Examiner*—P. J. Killos
*Attorney, Agent, or Firm*—G. F. Magdeburger; John Stoner, Jr.; W. Keith Turner

[57] ABSTRACT

A process for producing an alpha-hydroxy carboxylic acid which comprises contacting carbon monoxide with a saturated $C_2$–$C_{16}$ aldehyde, water, and a catalyst comprising hydrogen fluoride in a reaction zone and under conditions effective to form an alpha-hydroxy carboxylic acid, including a temperature between 0°C and 100°C and a carbon monoxide partial pressure between 10 and 4000 psig.

An alpha-alkoxy acid can be produced in the above reaction by using an alcohol instead of water.

12 Claims, 1 Drawing Figure

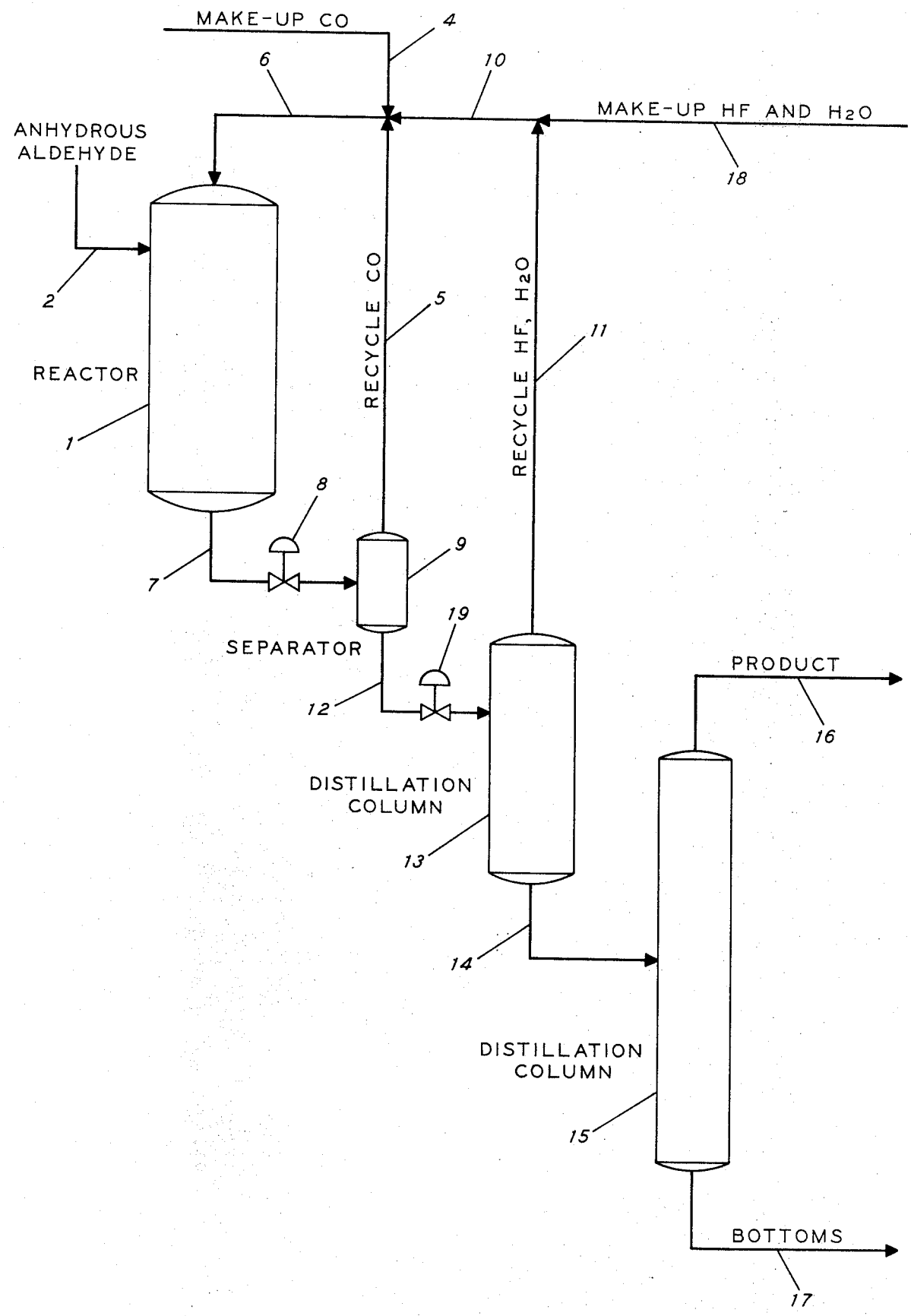

ALPHA-HYDROXY OR ALKOXY ACID PREPARATION

BACKGROUND OF THE INVENTION

The present invention relates to the reaction of carbon monoxide with a $C_2$ or higher aldehyde and water or an alcohol to produce an alpha-hydroxy carboxylic acid or an alpha-alkoxy carboxylic acid.

My related application Ser. No. 480,894, filed June 19, 1974, discloses a process for producing hydroxyacetic acid (commonly called glycolic acid) from carbon monoxide, formaldehyde, and water with a hydrogen fluoride catalyst.

My related application Ser. No. 532,563 entitled "Alkoxy Acid or Ester Preparation", filed on Dec. 13, 1974, discloses a process for producing alkoxy acetic acid from carbon monoxide, formaldehyde, alcohol, and water using a hydrogen fluoride catalyst.

U.S. Pat. No. 2,211,625 discloses the reaction of formaldehyde with carbon monoxide and an alcohol to produce an ester of glycolic acid in accordance with the following reaction:

$$HCHO + CO + ROH \rightarrow HOCH_2COOR$$

According to this patent, a catalyst such as hydrochloric, sulfuric, or phosphoric acid can be used.

U.S. Pat. No. 2,211,624 discloses the reaction of formaldehyde, carbon monoxide, and an acid such as acetic acid to obtain an alpha-acyloxy acid in accordance with the following reaction:

$$HCHO + CO + CH_3COOH \rightarrow CH_3COO-CH_2COOH$$

Acid catalysts for the reaction according to this patent include hydrochloric, sulfuric, and phosphoric acid.

U.S. Pat. Nos. 2,152,852, 2,153,064, and 2,265,945 disclose hydroxy-acetic acid production from formaldehyde, carbon monoxide and water using acid catalysts. U.S. Pat. No. 2,265,945 discloses as follows at Col. 1, lines 22–40:

"The above and other objects of the invention are realized by dissolving an aldehyde, having more than 1 carbon atom, or one of its polymers, in water, or a suitable solvent medium, and preferably in the presence of a catalyst having acidic characteristics, subjecting the resulting solution to heat and pressure and an atmosphere of carbon monoxide, whereupon a hydroxy acid is obtained in accordance with the equation: $RCHO+CO+HOH \rightarrow RCH(OH)COOH$ in which R may be hydrogen, an alkyl, aryl, aralkyl, cyclic or alicyclic group. Thus, for example, acetaldehyde yields lactic acid and the higher aldehydes, correspondingly higher hydroxy acids. This reaction may be carried out by placing the mixture of aldehyde, water and catalyst in an autoclave, applying the necessary pressure by forcing in carbon monoxide and effecting the reaction by the application of heat."

According to all three of these patents — that is, U.S. Pat. Nos. 2,152,852, 2,153,064 and 2,265,945 — the acid catalysts disclosed are hydrochloric, sulfuric, phosphoric and inorganic acid salts such as potassium acid sulfate, sodium acid phosphate and boron fluoride. Temperatures disclosed for use in the processes of the patents are 50° to 350°C and more preferably 140° to 225°C. Pressures disclosed are 5 to 1500 atmospheres (75 to 23,000 psi) and higher. In the examples of all 3 of the patents, the only inorganic acid catalysts used are phosphoric acid, sulfuric acid and hydrochloric acid. The temperatures used in the examples of the patents are usually between 160° and 200°C, and the pressures usually about 900 atmospheres (13,500 psi) and essentially always above 300 atmospheres (4500 psi). The severe reaction conditions indicated for the carbonylation of formaldehyde such as the high reaction temperature in the presence of corrosive acids and very high CO pressure require expensive equipment made from corrosion-resistant materials. According to the disclosures in the patents, the reaction can be effected in a continuous manner by passing the formaldehyde or its equivalent, water or its equivalent, and acid catalyst through a reaction zone either cocurrently or countercurrently to the flow of carbon monoxide.

SUMMARY OF THE INVENTION

According to the present invention a process is provided for producing an alpha-hydroxy or alkoxy carboxylic acid which comprises contacting carbon monoxide with a saturated $C_2$–$C_{16}$ aldehyde, water or an alcohol, and a catalyst comprising hydrogen fluoride in a reaction zone and under conditions effective to form an alpha-hydroxy carboxylic acid, including a temperature between 0° and 100°C and a carbon monoxide partial pressure between 10 and 4000 psig.

Among other factors, the present invention is based on my finding that unexpectedly moderate temperature and pressure are suitable for obtaining the specified products of the present invention, particularly products such as the alpha-hydroxy acid and alpha-alkoxy acid, when using hydrogen fluoride as a catalyst.

Whereas my earlier applications referred to above were particularly concerned with a formaldehyde feedstock, the present application is concerned with $C_2$ and higher aldehyde feedstocks. Preferred aldehyde feedstocks are $C_2$–$C_{16}$ saturated aldehydes, more preferably $C_2$–$C_6$ saturated aldehydes. The term "saturated" is used herein to connote that the R group attached to the aldehyde functional group is a saturated group — that is, an alkyl group.

I have particularly found that good yields of alpha-hydroxy propionic acid (commonly called lactic acid) are advantageously obtained by the process of the present invention wherein the aldehyde feedstock to the reaction zone is acetaldehyde.

Preferably the temperature in the reaction zone is between 20° and 60°C, and preferably the carbon monoxide partial pressure is between 10 and 3000 psig.

In accordance with a preferred embodiment, the aldehyde, water and hydrogen fluoride are fed to the reaction zone at a mol percent of 3–35% aldehyde, 3–35% water and 40–90% hydrogen fluoride, and the carbon monoxide partial pressure is maintained at 10–3000 psig in the reaction zone.

In accordance with another embodiment of the present invention, alpha-alkoxy acids are obtained by replacing the water in the above reaction with an alcohol. Preferred alcohols are $C_1$–$C_{20}$ primary alcohols or mixtures thereof, more preferably $C_1$–$C_{10}$ primary alcohols or mixtures thereof, and still more preferably the alcohol is methanol, ethanol, n-propanol, n-butanol, or a mixture thereof.

By using an excess of alcohol, the alpha-alkoxy acid can be converted to or is obtained mainly as alkyl alpha-alkoxy ester.

Similarly, the alpha-hydroxy acid obtained by reacting the aldehyde with carbon monoxide and water can be converted to alkyl alpha-hydroxy ester by reaction of the hydroxy acid with the appropriate alcohol.

According to a preferred embodiment for producing the alpha-alkoxy carboxylic acid, the aldehyde, alcohol and hydrogen fluoride are fed to the reaction zone at a mol percent of 3–35% aldehyde, 3–35% alcohol and 50–90% hydrogen fluoride, and the carbon monoxide partial pressure is maintained at 10–3000 psig in the reaction zone.

In accordance with another embodiment of the present invention, polyhydric alcohols can be reacted with the aldehyde and carbon monoxide. Depending on the quantity of aldehyde in the feed, one or more of the hydroxyl groups of the polyhydric alcohol will be etherified by capping with an alkyl carboxy methyl group, e.g.,

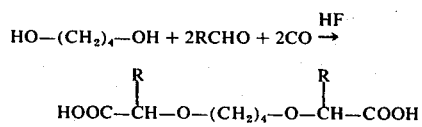

wherein R is an alkyl group having 1 to 15 Carbon atoms.

For complete reaction, there should be at least 1 mol of aldehyde per hydroxyl group.

Typical polyhydric alcohols include 1,4-butanediol, 1,3-propanediol, 1,8-octanediol, trimethylolpropane, pentaerythritol, 3-methyl-1,5-pentanediol, diethylene glycol, etc. Ethylene glycol may also be utilized in this reaction, in which case a cyclic ether ester is obtained from the reaction of 1 mol of aldehyde and 1 mol of ethylene glycol, as follows:

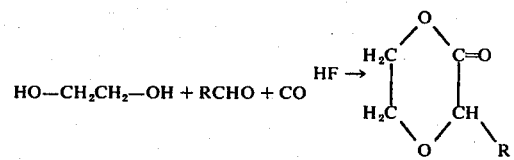

wherein R has the same significance as before.

In a further embodiment of the process for producing alpha-alkoxy carbooxylic acids, acetals or hemiacetals are used as the feedstock in lieu of both alcohol and aldehyde. Such compounds are produced by the acid-catalyzed reaction of an aldehyde and an alcohol:

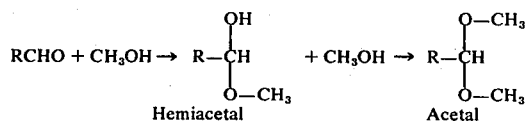

wherein R is as previously defined.

I have also found that a $C_2$–$C_{16}$ saturated aldehyde can advantageously be reacted with carbon monoxide and a carboxylic acid to obtain an alpha-acyloxy acid in good yields by using the hydrogen fluoride catalyst and reaction conditions as set forth above for water or alcohol feeds. Suitable carboxylic acids are $C_1$–$C_{10}$ carboxylic acids. $C_1$–$C_6$ saturated aliphatic carboxylic acids are preferred.

The terminology "$C_2$–$C_{16}$" and the like is used herein to mean that the referred-to material has from 2 to 16 carbon atoms.

THE DRAWING

In the embodiment of the process as shown in the drawing, water, carbon monoxide and hydrogen fluoride are combined and pass downwardly through a reactor to which anhydrous aldehyde is added. Excess feedstocks are recycled. The drawing is a simplified schematic process flow diagram illustrating one continuous process embodiment of the present invention to produce alpha-hydroxy carboxylic acids from the HF-catalyzed reaction of an aldehyde, carbon monoxide and water.

Referring to the drawing, make-up carbon monoxide is introduced via line 4 and is combined with recycle carbon monoxide introduced via line 5, and charged to reactor 1 via line 6. The recycle carbon monoxide stream also contains some aldehyde and hydrogen fluoride. At the same time, recycle hydrogen fluoride and water in line 11 are charged to the reactor via lines 10 and 6. Make-up hydrogen fluoride and water are added to the recycle stream via line 18. The reactor is maintained at about 25°–50°C and 1000–1500 psig. The product stream is removed through line 7, passes through letdown valve 8, and is charged to a separator vessel 9, maintained at about 50°C and a pressure below the reactor pressure, e.g., 900 psig. Here unreacted carbon monoxide is vaporized and sent back to the reactor via line 5. The product stream from the separator is next passed to stripper column 13 via line 12, which contains a pressure letdown valve 19. In the stripper column HF and water are distilled overhead at atmospheric or subatmospheric pressure and are recycled to the reactor through line 11. The bottoms are removed from the stripper via line 14. These bottoms consist of a mixture of alpha-hydroxy carboxylic acid and oligomers thereof.

Purification may be accomplished in several ways, usually by distillation, as shown in the drawing, wherein the bottoms from the stripper 13 are fed via line 14 into a distillation column 15. In this column, the product alpha-hydroxy carboxylic acid is distilled overhead and is removed via line 16. The bottoms, removed via line 17, may be hydrolyzed or treated in other ways to obtain products.

The crude product of line 14 may also be esterified, and the esters may also be separated by distillation and each fraction hydrolyzed to produce the alpha-hydroxy carboxylic acid.

The products of the process of the present invention are bifunctional in that they contain both a carboxyl and a hydroxyl or alkoxyl group. Many uses of these compounds are based upon this dual functionality. For example, the hydroxyl group may be oxidized to a carbonyl group to produce keto-acids such as pyruvic acid; either the hydroxyl or alkoxyl acid may be esterified and reduced to produce a 1,2-dihydroxy alkane or a 1-hydroxy-2-alkoxyalkane, respectively, both being desirable solvents and chemical intermediates; dehydration of the hydroxy acids of 3 or more carbon atoms produces alpha, beta-unsaturated acids which, after esterification or as is, are useful in making addition-type polymers; for chemical synthesis. The hydroxyl group is readily replaced by halogen upon reaction with phosphorus pentachloride. The first member of the series, lactic acid, is used as a reagent in glucose and pyrogallol analysis, as a food acidulant, in leather and textile treating, and as a pharmaceutical.

EXAMPLES

EXAMPLE 1

A 300-ml stainless-steel, magnetically stirred autoclave was charged with 4.8 g (0.3 mol) of water, 8.8 g (0.2 mol) of acetaldehyde, and 50 ml of hydrogen fluoride. The autoclave was pressured to 2000 psig with carbon monoxide. The reaction mix was stirred at 20°–27°C for 110 minutes. At the end of this time, the hydrogen fluoride was removed by distillation. The crude reaction mixture obtained in this way contained 25 mol percent yield (based on acetaldehyde) of lactic acid as determined by gas chromatography.

This example illustrates the process of the present invention, wherein carbon monoxide is the last feedstock to be charged to the reactor, a procedure which was eminently satisfactory with formaldehyde (Ser. No. 480,894). The next example illustrates a small yield improvement obtained by charging aqueous aldehyde to HF under carbon monoxide pressure.

EXAMPLE 2

The autoclave of Example 1 was charged with 50 ml of hydrogen fluoride and 1000 psig of carbon monoxide. Then a solution comprising 4.8 g (0.3 mol) of water and 8.8 g (0.2 mol) of acetaldehyde was pumped into the autoclave over a 50-minute time period. The resulting mixture was stirred at 20–27°C for an additional 60 minutes. The yield of lactic acid was 37% (molar).

The next example illustrates a preferred method of operation in which high yields are obtained by charging the aldehyde last, i.e., to a reactor already containing aqueous hydrogen fluoride under carbon monoxide pressure.

EXAMPLE 3

The procedure of Example 2 was followed except that 9.0 g (0.5 mol) of water was charged to the reactor along with 50 ml of hydrogen fluoride and 1100 psig of carbon monoxide. Acetaldehyde (8.8 g — 0.2 mol) was charged to this mixture over a period of 20 minutes. Reaction was continued at 20°–22°C for 60 minutes. Analysis showed an 80% (molar) yield of lactic acid.

EXAMPLE 4

The procedure of Example 3 was followed, except that the water was replaced by 9.6 g (0.3 mol) of methanol, and the reaction time was only 50 minutes. The product was alpha-methoxy propionic acid, obtained in 27 mol percent yield. The main by-product was a 16 molar percent yield of lactic acid.

EXAMPLE 5

The procedure of Example 3 was followed, except that the water was replaced by 12.0 g (0.2 mol) of acetic acid. The acetaldehyde was charged over a period of 13 minutes, and reaction was continued for another 56 minutes. Acetyl lactic acid was obtained in 9 percent yield.

The final example was carried out using a sulfuric acid catalyst (instead of a hydrogen fluoride catalyst as is required in the process of the present invention).

EXAMPLE 6

The same autoclave was charged with 32.4 g (1.8 mols) of water, 8.8 g (0.2 mol) of acetaldehyde, and 2 ml of sulfuric acid. The vessel was then charged with 1500 psig of carbon monoxide. The contents were stirred and heated as the temperature was raised from 22°C to 200°C over an 82-minute period of time. No lactic acid was produced, and the main product was polymeric.

I claim:

1. A process for producing an alpha-hydroxy carboxylic acid which comprises contacting carbon monoxide with a saturated $C_2$–$C_{16}$ aldehyde, water and a catalyst comprising hydrogen fluoride in a reaction zone and under conditions effective to form an alpha-hydroxy carboxylic acid including a temperature between 0° and 100°C and a carbon monoxide partial pressure between 10 and 4000 psig.

2. A process in accordance with claim 1 wherein the aldehyde is a $C_2$–$C_6$ aldehyde or mixture thereof.

3. A process in accordance with claim 1 wherein the aldehyde is acetaldehyde and the alpha-hydroxy carboxylic acid is lactic acid.

4. A process in accordance with claim 1 wherein the temperature is between 20°C and 60°C and the carbon monoxide partial pressure is between 10 and 3000 psig.

5. A process in accordance with claim 1 wherein the aldehyde, water and hydrogen fluoride are fed to the reaction zone at a mol percent of 3–35% aldehyde, 3–35% water and 40–90% hydrogen fluoride, and the carbon monoxide partial pressure is maintained at 10–3000 psig in the reaction zone.

6. A process for producing an alpha-alkoxy carboxylic acid which comprises contacting carbon monoxide with a saturated $C_2$–$C_{16}$ aldehyde, an alcohol and a catalyst comprising hydrogen fluoride in a reaction zone and under conditions effective to form an alpha-alkoxy carboxylic acid including a temperature between 0° and 100°C and a carbon monoxide partial pressure between 10 and 4000 psig.

7. A process in accordance with claim 6 wherein the aldehyde is a $C_2$–$C_6$ aldehyde or mixture thereof.

8. A process in accordance with claim 6 wherein the alcohol is a $C_1$–$C_{20}$ primary alcohol or mixture thereof.

9. A process in accordance with claim 8 wherein the alcohol is a $C_1$–$C_{10}$ primary alcohol or mixture thereof.

10. A process in accordance with claim 9 wherein the alcohol is methanol, ethanol, propanol, butanol, or mixture thereof.

11. A process in accordance with claim 6 wherein the temperature is between 20° and 60°C and the carbon monoxide partial pressure is between 10 and 3000 psig.

12. A process in accordance with claim 6 wherein the aldehyde, alcohol and hydrogen fluoride are fed to the reaction zone at a mol percent of 3–35% aldehyde, 3–35% alcohol, and 40–90% hydrogen fluoride, and the carbon monoxide partial pressure is maintained at 10–3000 psig in the reaction zone.

* * * * *